(12) United States Patent
Kagan et al.

(10) Patent No.: US 7,815,863 B2
(45) Date of Patent: Oct. 19, 2010

(54) CARTRIDGE FOR CONTAINING A SPECIMEN SAMPLE FOR OPTICAL ANALYSIS

(75) Inventors: Michael Kagan, Doylestown, PA (US);
Galla Chandra Rao, Princeton, NJ (US); Jerry Prohaska, Huntingdon Valley, PA (US); Tor Alden, Basking Ridge, NJ (US)

(73) Assignee: Veridex, LLC, Raritan, NJ (US)

( * ) Notice: Subject to any disclaimer, the term of this patent is extended or adjusted under 35 U.S.C. 154(b) by 1183 days.

(21) Appl. No.: 11/294,012

(22) Filed: Dec. 5, 2005

(65) Prior Publication Data

US 2006/0115380 A1    Jun. 1, 2006

Related U.S. Application Data

(62) Division of application No. 10/303,309, filed on Nov. 25, 2002, now Pat. No. 7,011,794.

(51) Int. Cl.
*B01L 3/00* (2006.01)
(52) U.S. Cl. .......................... 422/99; 422/102
(58) Field of Classification Search ................... 422/99, 422/102
See application file for complete search history.

(56) References Cited

U.S. PATENT DOCUMENTS

| 2,170,173 A | 8/1939 | Wheatley |
| 3,124,281 A | 3/1964 | Stull |
| 3,276,640 A | 10/1966 | Kessler |
| 4,427,138 A | 1/1984 | Heinlein |

(Continued)

FOREIGN PATENT DOCUMENTS

EP    0479448    4/1992

(Continued)

OTHER PUBLICATIONS

Tibbe, A. et al. "Cell Analysis Systems Based . . . " Cytometry, 43:31-37 (2001).

(Continued)

*Primary Examiner*—Jan M Ludlow

(57) ABSTRACT

An improved cartridge for holding a fluid sample with a small volume is disclosed herein. The cartridge has a test chamber and a vestibule through which the test fluids are inserted into the test chamber. Improved grips are flared-out to aid manipulation. The handle portion is reinforced to prevent flexing, and a prefabricated trough along the edge of the land surface prevents introduction of the adhesive into the region for analysis. The cartridge has a stopper having a dual sealing mechanism, which seals the test chamber inlet between the vestibule and the test chamber, and the mouth of the vestibule so that when the stopper is in place, the test chamber is closed to the admission of air or other contaminants. The vestibule is similarly closed against escape of the overflow from the test chamber. The stopper is composed of a single elastomer. An improved locking mechanism has two flexible walls on either side of the handhold that locks into their respective keepers on the cartridge to provide a secure lock. Additionally, an improved method for loading the cartridge allows for an even distribution of magnetically responsive particles contained within a fluid sample to be viewed in an array through the optically clear land surface portion of the cartridge.

4 Claims, 7 Drawing Sheets

Perspective view of stopper

U.S. PATENT DOCUMENTS

| | | | |
|---|---|---|---|
| 4,543,093 A * | 9/1985 | Christinger | ................ 604/228 |
| 4,569,464 A | 2/1986 | Wassilieff | |
| 4,849,173 A | 7/1989 | Chang | |
| 4,859,610 A | 8/1989 | Maggio | |
| 4,933,291 A | 6/1990 | Daiss | |
| 5,026,526 A | 6/1991 | Quenin | |
| 5,089,417 A | 2/1992 | Wogoman | |
| 5,149,506 A | 9/1992 | Skiba | |
| 5,179,862 A | 1/1993 | Lynnworth | |
| 5,211,313 A | 5/1993 | Lucking | |
| 5,246,669 A | 9/1993 | Hayashi | |
| 5,277,873 A | 1/1994 | Hsei | |
| 5,302,348 A | 4/1994 | Cusack | |
| 5,578,269 A | 11/1996 | Yaremko | |
| 5,658,801 A | 8/1997 | Poissant | |
| 5,714,123 A | 2/1998 | Sohrab | |
| 5,772,966 A | 6/1998 | Maracas | |
| 5,780,304 A | 7/1998 | Matzinger | |
| 5,795,543 A | 8/1998 | Poto | |
| 5,799,829 A | 9/1998 | Lier | |
| 5,800,781 A | 9/1998 | Gavin | |
| 5,814,275 A | 9/1998 | Lewis | |
| 5,814,277 A | 9/1998 | Bell | |
| 5,882,942 A | 3/1999 | Kagaya | |
| 5,958,349 A | 9/1999 | Petersen | |
| 5,985,153 A | 11/1999 | Dolan | |
| 6,013,188 A | 1/2000 | Terstappen | |
| 6,013,532 A | 1/2000 | Liberti | |
| 6,184,040 B1 | 2/2001 | Polizzotto | |
| 6,239,445 B1 | 5/2001 | Shaeef | |
| 6,271,046 B1 | 8/2001 | Chandler | |
| 6,342,183 B1 | 1/2002 | Lappe | |
| 6,861,259 B2 * | 3/2005 | Columbus | ...................... 436/3 |
| 2002/0109838 A1 | 8/2002 | Columbus | |

FOREIGN PATENT DOCUMENTS

| | | | |
|---|---|---|---|
| WO | PCT/US02/04124 | | 8/2002 |
| WO | WO 02/065103 | * | 8/2002 |

OTHER PUBLICATIONS

Tibbe, A. et al. "Optical Tracking and Detection . . . ," Nature, 17:1210-1213, (1999).

EP Search Report For Application EP 03 78 6902 Date of Completion Feb. 28, 2006.

* cited by examiner

Cartridge chamber and receptacle

Front View of stopper in place

Front View of stopper removed

Cross-sectional view (A.) and magnified cross-sectional view (B.)
and longitudinal section view (C.)

A.

B.

C.

Cooperation between the cartridge body and the stopper

Perspective view of stopper

Enlarged view of stopper engaged with the body of the cartridge

CARTRIDGE FOR CONTAINING A SPECIMEN SAMPLE FOR OPTICAL ANALYSIS

CROSS-REFERENCE TO RELATED APPLICATIONS

This application is a divisional of Ser. No. 10/303,309, filed Nov. 25, 2002 now U.S. Pat. No. 7,011,794, now allowed.

FIELD OF THE INVENTION

The present invention is an improvement upon an earlier filed application relating to a cartridge having a chamber for containing a specimen sample used in optical analysis (PCT/US02/04124; U.S. Pat. No. 6,861,259; U.S. Ser. No. 10/988,057). One improvement enables the use of the cartridge in a manner that is more practical and less expensive for analysis of small biological samples, particularly blood. Another improvement enables a more efficient and uniform distribution of magnetically labeled target components within a sample prior to analysis.

BACKGROUND OF THE INVENTION

When performing optical analysis on specimens in liquid suspension, it is customary to discard the specimen after analysis. For rare cells, however, it is often desirable to preserve the liquid specimen for further testing or for use in further procedures. In certain procedures, it is desirable to select a specimen of a relatively small sample (less than 400 ul) from larger volumes (up to 100 ml), and it is likely that the volume of the specimen, which may be extracted from such a sample, is limited, making it especially important to avoid destruction of the specimen or any substantial part thereof. It is likewise important to avoid contamination of the specimen and to avoid conditions leading to deterioration of the specimen or impairment of analysis.

One cause of inconsistent optical analysis from sample to sample is a lack of uniform distribution of the magnetic particles and the magnetically labeled target components within the fluid sample due to gravitational forces. This pooling affect occurs when the sample is first placed into the cartridge chamber. Unless the chamber is perfectly horizontal, the magnetic particles, together with the magnetically labeled target components tend to settle toward the lower portions of the chamber. When the chamber is loaded in the vertical position, a preferred loading position, the magnetic particles and the magnetically labeled target components settle toward the distal portion of the chamber. Consequently, the magnetic particles and the magnetically labeled target components do not distribute uniformly across the optical window, causing the inability to perform optical analysis.

Another issue in the development of the cartridge and stopper is to provide a structure that is relatively inexpensive to manufacture (PCT/US02/04124), yet functions satisfactorily in preserving the sample. Construction, from two different plastic materials such as that described in the stopper component of the parent application, are expensive to manufacture and complicated in their construction. Since specimen samples are stored in a manner to prevent deterioration, there also is a need to maintain the locking feature so as to provide a proper seal against contamination and air. Thus, a stopper that would incorporate the benefits of a single elastomer composition together with a locking mechanism to minimize deterioration of the sample is needed.

In conjunction with a need to improve sample storage for optical analysis, there is a need to increase the ease and speed of manipulations of the cartridge. A better grasp on the cartridge would prevent unnecessary cartridge flexing that could allow air to enter the test chamber, and would provide more secure transfer of the cartridge from the loading position to the platform for analysis.

SUMMARY OF THE INVENTION

As can be seen from the discussion, above, there is a need to further improve upon select aspects of US Patent Application PCT/US02/04124. The present application describes a collection chamber designed to isolate a small sample for analysis and to preserve the sample for additional testing. Specifically, this collection device enables the exclusion of air as bubbles or other forms from the sample chamber, but does not provide a low cost chamber with uniform analyte distribution for analysis.

U.S. Pat. No. 5,246,669 discloses a sampling device for collecting a small sample and mixing it with a test liquid. In this patent, the device provides a pickup device, which extracts a small sample from a larger quantity of solid or semi-solid material to be tested. The device separates the small sample from the residue and isolates the residue so as to avoid contamination of the small sample or the surrounding atmosphere. The device does not provide for salvaging either of the test sample or the residue and does not have any provision for excluding air in the form of bubbles from the test liquid.

In addition to the need to redesign the cartridge and stopper, improved optical analysis is also obtained in the manufacturing process of the cartridge of the invention. There is a need to manufacture a cartridge that allows for a consistently clear and uniform area for viewing. The sample would circumvent problems in the analysis of magnetically labeled target components, particularly with respect to those target components located close to the contact area between the cartridge dome and the optically clear land surface interface. More specifically, interference from adhesive used to join the optically clear land surface with the rest of the cartridge results when the adhesive spreads onto the optical path during the manufacture of the chamber. Thus, there is a need to develop a process for affixing the optically clear land surface in a way that prevents the introduction of adhesive onto the optical analysis region.

Improving the ability to manipulate a chamber containing magnetically labeled target components within a sample coupled with the ability to display them in a uniform manner, all in a low cost manner, enables the present invention to provide a consistent platform for optical analysis.

Accordingly, the present invention provides an improvement to a novel cartridge for use in optical analysis of specimens. As with the original cartridge, the improved version has a test chamber that contains the specimen for subsequent procedures, provides a platform for optical analysis of the specimen without loss of any substantial part thereof, and enables the specimen to be retained in the cartridge test chamber in the absence of air bubbles or other contaminants. The cartridge is also used in a method for handling specimens enabling the specimen to be presented in a test chamber for optical analysis without the risk for loss of any substantial part of the specimen and without the risk of inclusion of air bubbles or exposure to other deteriorating conditions in the test chamber with the target components evenly distributed for optical analysis.

BRIEF DESCRIPTION OF THE DRAWINGS

FIGS. 4A and 4B are cross-sectional views taken on the line 4A-4A of FIG. 3. FIG. 4B is an enlarged cross-sectional view of the adhesive trough on the edge of the shelf portion of the body juxtaposed to the optically clear edge of the land surface. FIG. 4C is a longitudinal-section taken on the line of 4B-4B of FIG. 3.

FIG. 5A shows the stopper removed with the specimen in place within the chamber and the vestibule. FIG. 5B is a view similar to FIG. 5A showing the penetration of the probe of the stopper into the buffer within the vestibule. FIG. 5C shows the stopper in place closing both the port between the chamber and the vestibule and the upper end of the vestibule.

DETAILED DESCRIPTION OF THE INVENTION

Figure 1:
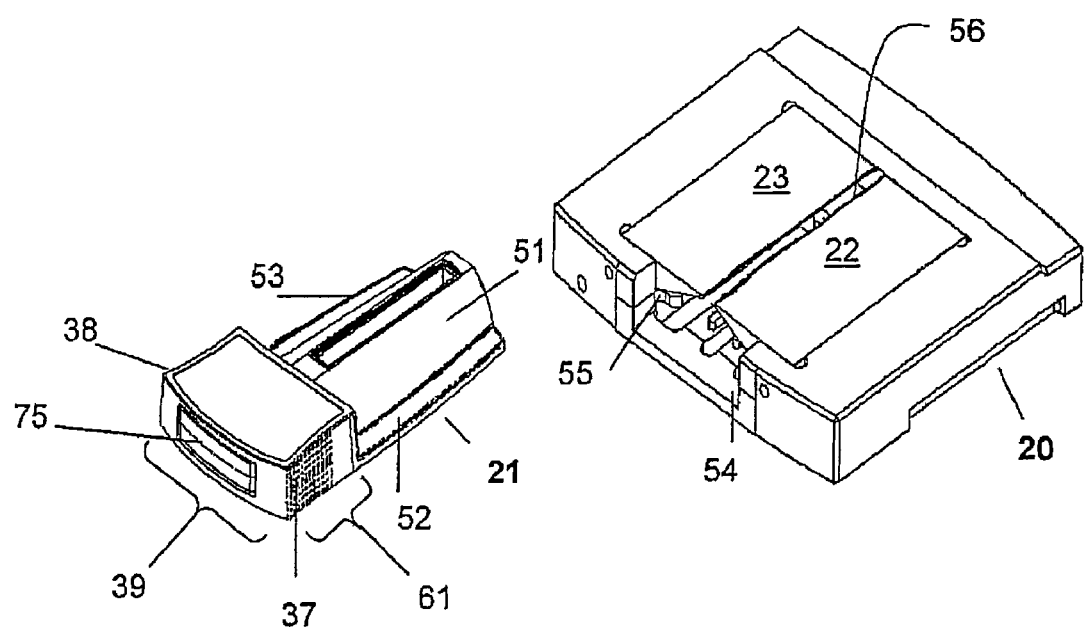
FIG. 1 is a schematic representation of the cartridge and receptacle having a pair of opposed magnetic poles made in accordance with the present invention.

The device of the present invention has been improved to limit significant settling of target components prior to loading, thus enabling a uniform distribution of the array of magnetically responsive particles and magnetically labeled target components along the viewing surface. Because the biological sample is loaded into the cartridge in the presence of a magnetic field, an equal distribution of magnetically labeled target components is ensured. Loading is accomplished by placing the cartridge vertically within a magnetic field prior to sample loading. The sample is then introduced into the cartridge chamber, closed with a stopper, and maintained until analyzed. Optical analysis is completed without settling and with a uniform distribution of target components that remains consistent from sample to sample.

As with the cartridge from the parental application, the specimen sample can be introduced into the test chamber of the cartridge along with a buffer solution in which the respective properties of the specimen and the buffer solution are such as to provide an interface separating the buffer solution from the sample. The sample chamber is elongated with a port at one end. Preferably, the buffer solution is of a density less than or equal to the density of the sample so that when the chamber is disposed with the ported end upright, the buffer solution is positioned above the interface and the sample is positioned below the interface. During the filling of the chamber, any air or other contaminants, which are less dense than the buffer solution, are allowed to gravitate upwardly through the buffer solution towards the port in the upper end of the chamber. The chamber is designed with a vestibule containing an overflow reservoir capable of being sealed both from the test chamber and the exterior environment. A stopper is provided for sealing both ends of the vestibule through its attached probe, which extends into the buffer solution above the interface. As the stopper, through the probe, is engaged with the port of the test chamber, the probe displaces the buffer into the vestibule. The stopper now forms a primary seal, which closes the test sample chamber from the vestibule. Subsequently, the stopper forms a second seal to close the outside entrance of the vestibule to prevent escape of the buffer from the vestibule. The vestibule thus serves as an overflow receptacle. The first seal closes the test chamber after any deleterious air bubbles in the chamber have migrated into the vestibule. Thereafter, the second seal closes the overflow chamber to retain the buffer solution against loss with the simultaneous engagement of the stopper through an improved clip mechanism.

Improvements on the stopper results in reduced expense and increased ease of cartridge handling. The improved stopper is composed of a single elastomer with a preferred durometer value of about 60 to 90. The stopper is locked into position in the cartridge by flexible walls so that when the second seal closes the overflow chamber the walls are compressed until they snap outwardly to position against their respective keeper elements. This interaction allows the stopper to lock into place, making stopper alignment with the chamber easier and making the stopper much more difficult to remove after filling.

When in place, the stopper and handle permit the cartridge to be griped and manipulated into position with the optical detecting device in an orientation which positions the test chamber so that the target cells are in a suitable position within the field of observation for the detection equipment.

Grips on the cartridge used for manipulating the cartridge into position have been improved by flaring-out the inward taper to allow a more secure grasp and better control. Accordingly, the cartridge may be easily mounted in a microscope or other detection equipment to allow positioning of the target components in the biological sample within the equipment's sample observation field. Within the handle portion and between the grip areas, the cartridge has improved support to prevent unintentional flexing thereby affecting the established seals between the stopper and cartridge.

Finally, a novel type of manufacture for the attachment of the optical land surface to the plastic portion of the cartridge is described. More specifically, a plastic edge is in contact with an optically clear land surface, which is usually glass. The edge is shaped as a small shelf to seat the land surface. The shelf spans the entire area to be in contact with the land surface. A small trough is positioned along the shelf, but within the area to be in contact. A binding adhesive is introduced into the trough and along the entire contact region. The binding adhesive is an optically clear adhesive that is non-fluorescent and unable to react with the sample. When the optically clear land surface is placed in contact with the shelf, the adhesive is channeled away from the optical path. This allows for a more reproducible and for a more consistent observation during optical analysis. While any adhesive with the characteristics described above will work, adhesives can be of a pressure-sensitive type, heat cured type, or activated by ultraviolet light.

Optical analysis of biological samples, especially rare cells, requires a method and means to maintain the specimen in a condition that would allow inexpensive and reproducible. The improved sample cartridge and stopper, when used together, are designed to avoid contamination of the biological sample, but with an improved design and manufacture which allows for better control during any manipulation prior to optical analysis, uniform distribution of magnetically labeled target components for optical analysis, and at a lower cost to produce.

One improvement in the preparation of the sample is to load and store the cartridge assembly, either the parental or improved version, within an applied magnetic field prior to sample filling and optical analysis. The cartridge is positioned vertically before loading within an applied magnetic field in preparation for sample loading. The sample is introduced into the cartridge chamber within the magnetic field, resulting in the prevention of any settling of magnetically responsive particles and any magnetically labeled target components. Accordingly, the magnetically labeled target components are arranged in an evenly distributed, which is consistently displayed from sample to sample. The magnetic field prevents these same magnetically labeled target components from clustering within one region of the cartridge prior to optical analysis. Thus after insertion of the stopper into the cartridge, the magnetically labeled target components of the biological sample will remain stably positioned along the flat land surface of the cartridge until removed from the magnetic field after analysis.

The cartridge and stopper of the improved invention are particularly adapted for use in a detecting apparatus such as shown in U.S. Pat. No. 6,013,532, which issued to Liberti et al. on Jan. 11, 2000, and described in a paper entitled "Optical Tracking and Detection of Immunomagnetically Selected and Aligned Cells" by Arjan G. J. Tibbe et al., Published in *Nature Biotechnology*, Vol. 17, December 1999, pp 1210-1213, both of which are incorporated by reference herein. The cartridge and receptacle, shown schematically in FIG. 1 of the patent, is effective to immobilize magnetically labeled target entities, such as cells, within a fluid medium for observation, analysis or manipulation. The magnetically labeled target entities are deposited in a test chamber where they are manipulated by a magnetic field to dispose the magnetically labeled target entities in a monolayer along a wall of the test chamber. A discussion of automated magnetic separation techniques is included in U.S. Pat. No. 5,985,153 which issued to Gerald J. Dolan et al. on Nov. 16, 1999, and in a paper entitled "Cell Analysis System Based on Immunomagnetic Cell Selection and Alignment Followed By Immunofluorescent Analysis Using Compact Disk Technologies" by Arjan G. J. Tibbe et al., published in *Cytometry*, 43:31-37 (2001), both of which are also incorporated herein by reference.

Referring to FIG. 1, an improved cartridge embodying the invention is shown at 21 mounted in a receptacle 20 having a pair of opposed magnetic poles, 22 and 23 which have a gap formed therebetween. In the illustrated detecting apparatus, the receptacle 20 is positioned horizontally in the path of the optical system of the apparatus with the gap upwardly, but for other applications the receptacle may be positioned vertically. In FIG. 1, the lower surfaces of the poles 22 and 23 are tapered toward the gap so that magnetic field applied to the chamber is non-uniform and has a substantially vertical gradient effect directed toward the gap transverse to the longitudinal axis of the cartridge 21 to urge magnetically-responsive particles and magnetically labeled targets within the chamber towards the wall of the cartridge which is substantially co-planar with the gap. The magnetically labeled target entities are displayed as an orderly monolayer on the interior surface of the test chamber, and an automated observation system can be configured to provide relative motion between the cartridge and the light-gathering elements of the observation system in order to tract the collected magnetically labeled target entities for automated enumeration, which can include spectral analysis of light emitted, absorbed or scattered by the collected magnetically labeled targets.

The complete system comprises optical tracking beam analysis components similar to those employed for reading compact discs known in the audio and data storage arts (see PCT/US02/04124). Briefly, a pair of laser diodes generates parallel beams of light. One beam is employed by the analysis system (not shown) for locating and tracking lines of the target entities. The other beam is used for detecting the presence of collected target entities adjacent to a located line. Relative motion between the cartridge and the optical elements of the analysis system is provided by a mechanical translation unit (not shown). Coordination of the functions of the analysis system is provided by a microprocessor (not shown). The tracking beam, which is reflected by dichroic mirror through the aperture is focused upon the upper surface of the cartridge by an objective lens. The dichroic mirror 7 through the dichroic lens and the objective lens reflects the detecting beam.

Light reflected by the tracking lines and the target entities will be transmitted through dichroic mirrors and toward a photo detector (not shown). The detector generates a data signal, which is fed to the microprocessor for the unit, as described more fully in the above-mentioned U.S. Pat. No. 5,985,153, to control the translation of the unit and process the data provided by the detector.

The improved cartridge 21 may also be used in other detecting apparatus such as a microscope, as described in the above-mentioned U.S. Pat. No. 6,013,532, in which the stage is designed to receive the receptacles 20 so as to position the surface of the cartridge in the light path of the microscope. As noted above, the orientation of the test chamber may be horizontal, vertical or at any angle determined by the instrumentation of the detecting apparatus.

As shown in the orientation of FIG. 1, the improved cartridge 21 has a domed body portion 51 having outwardly projecting glides 52 and 53 on opposite sides thereof. While holding the cartridge by the grips 37 38, the glides 52 and 53 are designed to slide into guide ways 54 and 55 in the receptacle so that the domed body portion of the cartridge underlies the lower surfaces of the poles 22 and 23. Intermediate between the guide ways 54 and 55, the receptacle has a slot 56 providing an optical path through the bottom of the receptacle. The optical path registers with the longitudinal centerline of the cartridge when the cartridge is inserted into position within receptacle 20.

Figure 2:
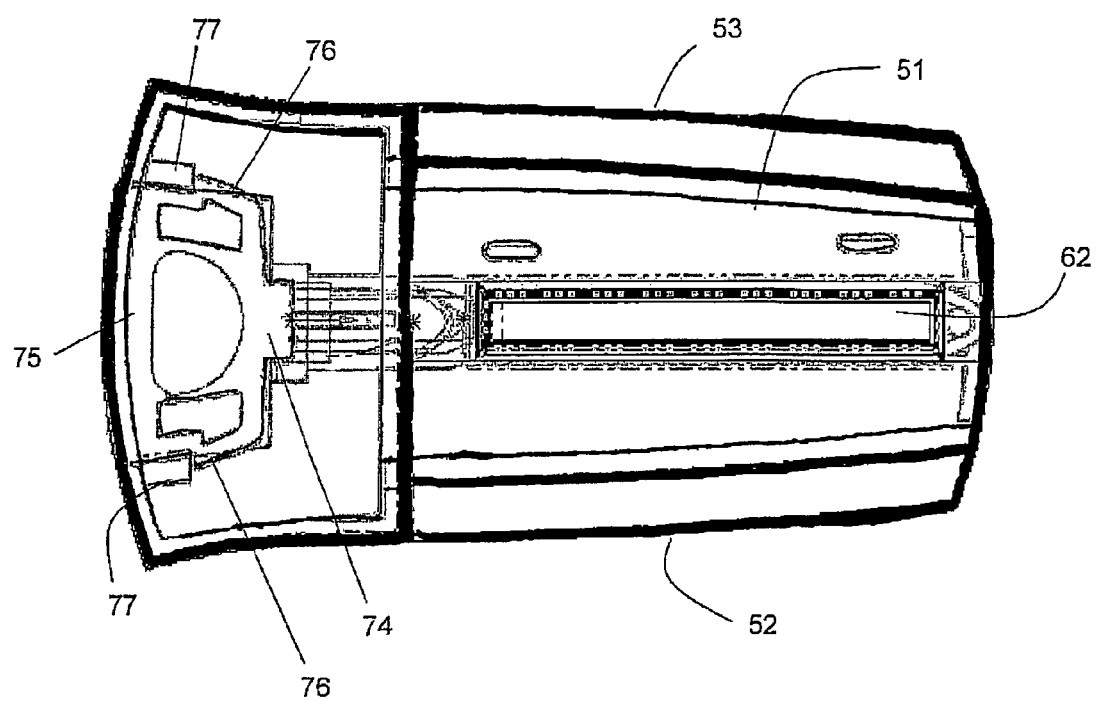
FIG. 2 is a front view of a cartridge embodying the present invention and the associated improvements with its stopper in place to illustrate the engagement of the stopper with the body of the cartridge.

FIG. 2 shows the cartridge 21 in front view embodying the present invention and the associated improvements with its stopper in place to illustrate the engagement of the stopper with the body of the cartridge. The stopper is shown with plug 74 sealingly engage. With the stopper fully inserted, the plug 74 closes the proximal end of the vestibule. The stopper has an improved handhold 75 and an improved locking mechanism composed of two flexible walls 76, 76. The flexible walls 76, 76 flank the plug 74 and engage their respective keeper elements 77, 77 also improved and located in the handle portion 61 of the cartridge. The improved keeper elements are supported at the top of the handle portion and laterally along the sides of the keeper elements. This provides extra rigid support when engaged as shown.

Figure 3:
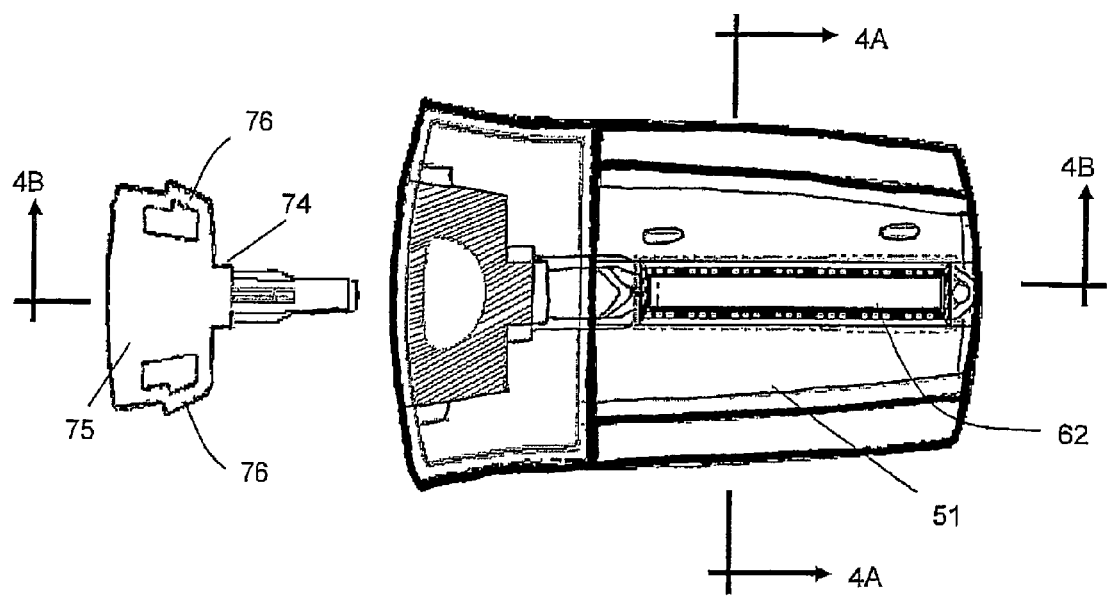
FIG. 3 is a view similar to FIG. 2 showing the stopper removed from the body of the cartridge.
Figure 4:
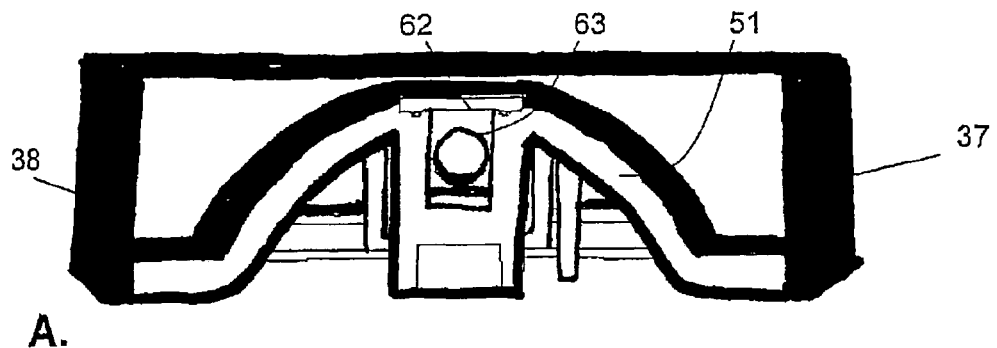
FIG. 4 is a cross-sectional (A), magnified cross-sectional (B), and longitudinal-sectional (C) view.
Figure 4:
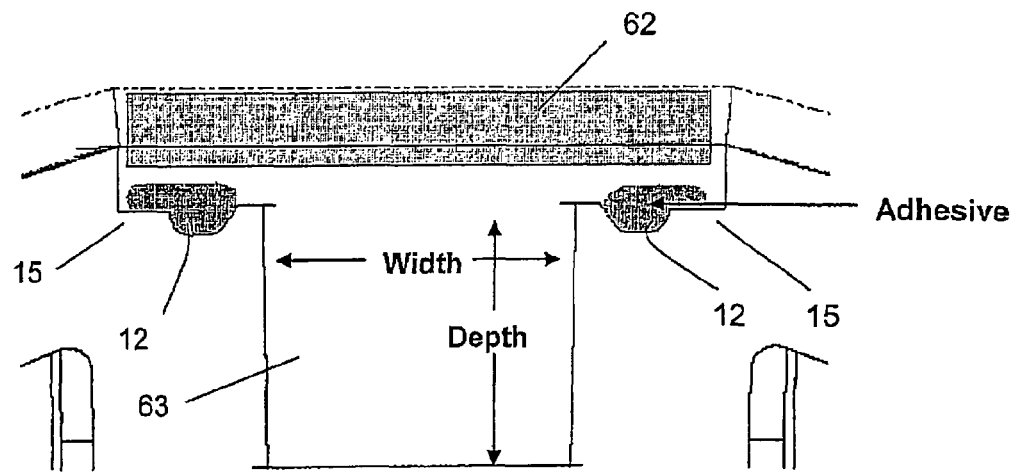
Figure 4:
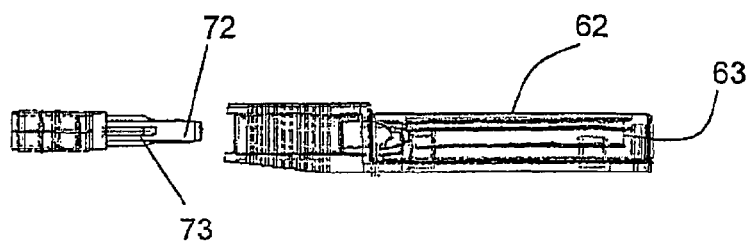

FIG. 3 shows the cartridge 21 in front view embodying the present invention and the associated improvements with its stopper removed to illustrate the difference when not engaged with the body of the cartridge The improved cartridge is formed from a non-magnetic inert material, such as polycarbonate, polystyrene or acrylic with no fluorescent additives and is formed to provide a rigid chamber, which may be manipulated into and out of the optical path of the optical analysis system. A sectional view with the stopper removed shows the cartridge with flanking grips 37, 38 and a centrally located flat land surface 62 formed from optically clear material such as glass and affixed at the top of the dome 51 (FIG. 4A).

A procedure for affixing the optically clear land surface 62 to the cartridge is incorporated into the embodiment to provide better adhesion (see FIG. 4), a more consistent orientation of the land surface 62 with respect to the viewing aperture, but most importantly less interference with optical analysis due to excess adhesive in the chamber area. The procedure allows for a more even and controlled application of the adhesive along the interface between the land surface 62 and the top of the non-magnetically inert dome 51. More specifically, the improved affixation prevents the adhesive from spreading in both lateral directions by forcing adhesive away from the chamber area.

Basically, the improvement is in the geometry of an adhesive trough 12, which is designed to channel the adhesive away from the chamber area when the flat land surface is attached (FIG. 4B). The molded inert material of the cartridge dome is shaped as a small shelf 15 at the edge to form the contact area with the flat land surface 62. A small trough, filled with adhesive, runs along the edge. The trough spans the entire contact area so that when the flat land surface is placed on the edge, contact is made with the adhesive. The adhesive is allowed to wick down the trough and across the contact area. This area is then exposed to UV light, heat cured, or treated by any means to securely bond the edge to the land surface. The preferred embodiment is to use a UV light adhesive to bond 0.5 mm thick glass cut to tight tolerances with molded plastic. The molded plastic must be non-fluorescent, rigid, optically clear, and non-reactive with the sample. Typical examples are polycarbonate or polystyrene.

The land surface 62 is optically clear and permanently affixed to the cartridge. Thus when positioned in the receptacle 20, the test chamber 63 is aligned with the aperture 56 of the receptacle along the light path of the detecting apparatus in which receptacle 20 is mounted. This provides for an optimum analytical viewing surface.

Figure 5:
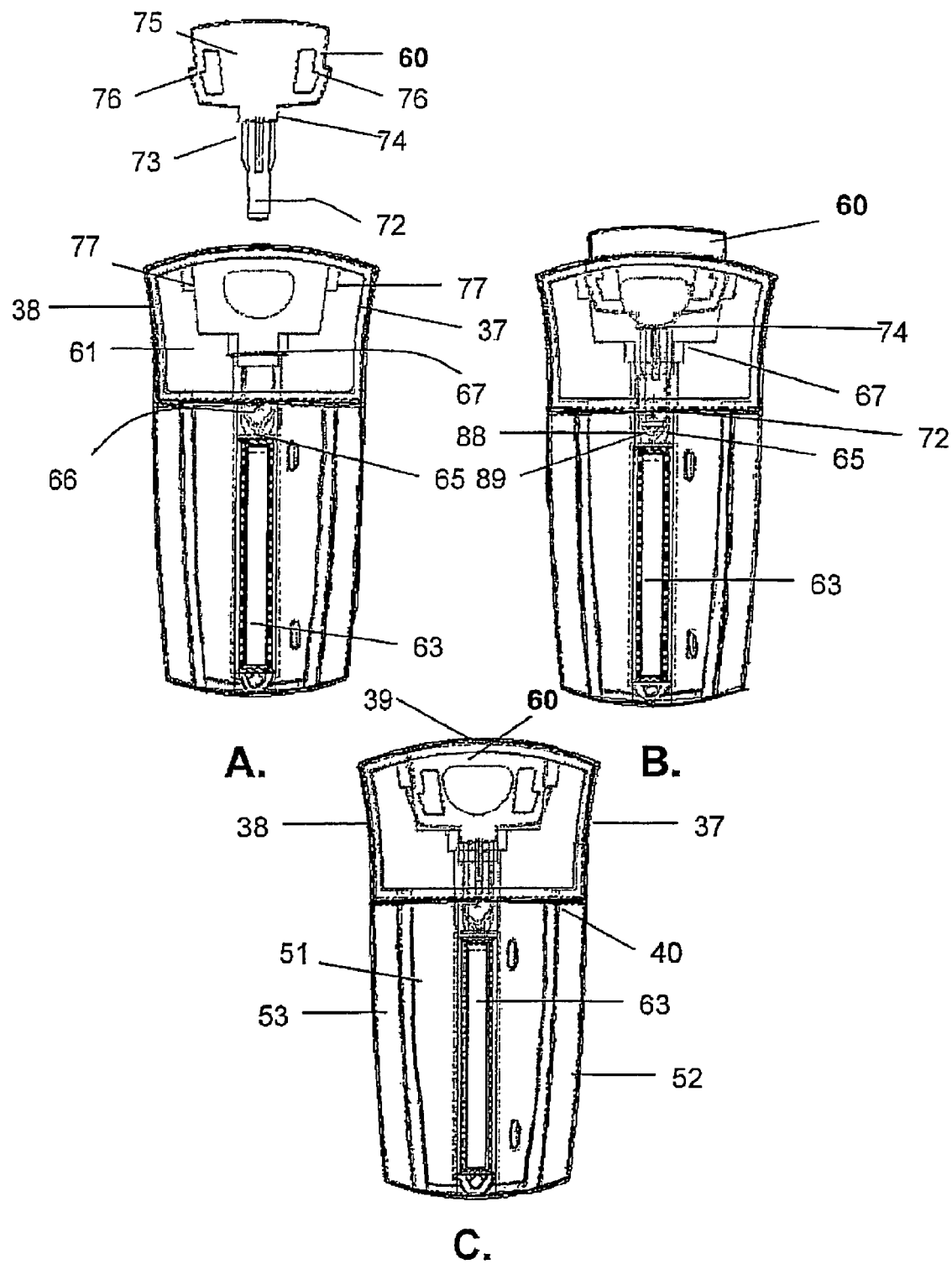
FIGS. 5A, 5B, AND 5C are sectional views of the cartridge in loading position illustrating the cooperation between the cartridge body and the stopper to entrap the specimen in the cartridge in the absence of air.

The test chamber 63 is closed at the distal end remote from the handle portion 61 and has an inlet opening 65 at the proximal end adjacent the grips 37, 38 (FIG. 5A). The inlet 65 is positioned in the center of the end wall of the test chamber 63 at the proximal end so that when the cartridge is disposed vertically for filling the inlet opening 65 is at the uppermost part of the chamber 63. The body of the cartridge provides a vestibule chamber 66 having an enlarged mouth 67 at its entrance end. The vestibule chamber 66 communicates with the test chamber 63 through the inlet opening 65. Between the mouth 67 and the inlet 65, the vestibule 66 provides an overflow reservoir, as described more fully hereinafter.

The test chamber 63 is adapted to be closed by the plunger 71 of an improved stopper having a probe 72 adapted for sealing through an engagement with the inlet 65 of the test chamber 63. Rearwardly of the probe 72, the stopper has a ribbed stem 73. The ribbed stem terminates into a plug 74, which is adapted to sealingly engage in the mouth 67 as the stopper is fully inserted through the vestibule 66. When fully inserted, the plug 74 closes the proximal end of the vestibule 66. Beyond the plug 74, the stopper has an improved handhold 75 and an improved locking mechanism composed of two flexible walls 76, 76. The flexible walls 76, 76 flank the plug 74 and engage their respective keeper elements 77, 77 also improved and located in the handle portion 61 of the cartridge. The improved keeper elements are supported at the top of the handle portion and laterally along the sides of the keeper elements. This provides extra rigid support when engaged. When the flexible walls of the stopper 76, 76 are engaged, they are compressed as they are pushed by the improved keeper elements 77, 77, but then snap outwardly when finally in place.

The improved cartridge has a handle portion 61 with associated grips enabling the insertion and removal of the cartridge into and out from the receptacle. The handle portion 61 has also been improved by flaring the side grips 37, 38 located orthogonal to the first face. The grip area is made to flare away from the radial axis of the cartridge. The handle portion has an arch-like extension on a first face. The first face is located on the domed side of the body. This face includes the domed body portion 51 with projecting guides 52 and 53 of the cartridge and the first face of the hand portion 61, defined along an upper edge of improved grips 37, 38, a curved upper edge of the arch-like extension 39, and the upper edge 40 which forms a border above the domed body portion 51 of the cartridge. A second face of the handle is opposite the dome body, and contains an inner-framed structure bounded along the radial axis of the cartridge by the two keeper elements 77, 77 and along a longitudinal axis by the uppermost portion of the handle and the enlarged mouth 67 of the vestibule. Changes to both faces provide a more secure lock for the stopper when engaged in position, and a much-improved rigid support for cartridge manipulation.

The projecting part of the stopper including the probe 72 and the plug 74 comprise an elastomeric material such as a thermoplastic elastomer (DYNAFLEX®), or other elastomeric material capable of forming seals with the inlet 65 and the mouth 67, respectively. The elastomeric material must also be non-fluorescent and non-reactive with the sample. The durometer of the elastomeric material is in the range of about 60 to 100 with a more preferred range of about 80 to 90 and the most preferred about 90. The handhold 75 of the stopper and the flexible walls 76, 76 are formed of the same elastomer as the probe and plug, thus making the entire stopper composed of a single elastomer. As with the parental cartridge/stopper, there is little ability to twist the stopper handhold 75 about its axis, especially after the flexible walls are securely locked into place. To release their engagement with the keepers 77, 77, a window within the framed area of the cartridge handhold 61 allows access for manual compression of the flexible walls and reversal of the engagement. Overall, this single elastomer design provides for a lower cost cartridge/stopper assembly.

As shown in FIG. 4C, the cartridge is disposed with its longitudinal axis horizontal so that the flat land area 62 of the test chamber 63 is disposed within the field of observation of the detection equipment. When filling the test chamber 63, the cartridge is disposed with its longitudinal axis upright with the vestibule 66 disposed above the test chamber 63.

As shown in FIGS. 5A to 5C, a test liquid is introduced into the test chamber 63 along with any associated buffer solution. The buffer solution has a density which is less than or equal to the test liquid so that there is a liquid interface provided between the two solutions. The volume of the buffer solution is sufficient to completely fill the test chamber 63. The filling operation excludes air from the test chamber 63, and any air bubbles remaining in the buffer solution will gravitate upwardly through the inlet 65 into the vestibule 66.

The construction and arrangement of the chamber insures that air bubbles are excluded from the test chamber and pressure build-up in the unit is avoided. As shown in FIGS. 5A to C, when the stopper 60 is inserted into the vestibule, a projecting portion containing the probe 72 displaces the buffer solution as it enters the established fill line and causes the surface of the buffer solution to rise within the vestibule until the probe 72 contacts the inlet 65. As shown, the inlet 65 has a flared mouth 88 and a cylindrical channel 89 below the flared mouth (FIG. 5B). At this point, the surface of the buffer solution is shifted upwardly to an elevated fill line. Further movement of the stopper downwardly causes the tip of the probe 72 to enter the channel 89 of the inlet 65. When the probe 72 engages the cylindrical channel 89, the probe affects a first seal, closing communication between the test chamber 89 and the vestibule 66. Further penetration of the probe 72 into the cylindrical portion of the cylindrical channel 89 of the inlet 65 perfects the seal (FIG. 5C). Because the tip of the probe 72 closes the cylindrical channel 89, and, in the present instance, the internal diameter of the channel 89 of the inlet 65 is less than the internal dimensions of the chamber 63 so that the volume of buffer solution in the channel is minimal, and the engagement of the probe 72 into the channel 89 when effecting the first seal does not significantly increase the pressure within the test chamber 63. The vestibule remains open at the top until the plug 74 enters the mouth 67, allowing the vestibule to remain at ambient pressure.

The design of the present invention may be used for any analysis chamber, but it has been specifically created for analysis chambers for testing extremely small samples having a volume of less than 1 ml. In the illustrated embodiment, referring to FIG. 4B, the width of the chamber 63 below the land area 62 is approximately 3 mm and the depth is approximately 4 mm, providing a cross-sectional area in the range of 10 to 14 square millimeters. The length along the longitudinal axis is approximately 30 mm. The volume of the chamber 63 should be in the range between 22 ul and 675 ul, preferably at least 315 ul. The diameter of the inlet 65 is in the range between 0.0381 mm and 3.18 mm, and preferably is 2.35 mm, providing a flow area of approximately 10 square millimeters. Beyond the inlet 65, the vestibule flares out, in this case to a diameter of 4.23 mm, and extends approximately 14 mm to the mouth 67, which, in this case, has a width of 6.3 mm. With the plug fully inserted, the volume of the vestibule 66 is preferably at least 95 ul. The width of the test chamber at the upper wall is slightly more than the diameter of the channel 89 of the inlet 656. Although not shown in the figures, the corners around the perimeter of the upper wall are broken or beveled, so as to avoid entrapment of any air bubbles gravitating upwardly through the chamber 63. The bevel is preferably at an angle of between 2° and 30° relative to the longitudinal axis of the chamber 63 and the inlet 65.

Figure 6:
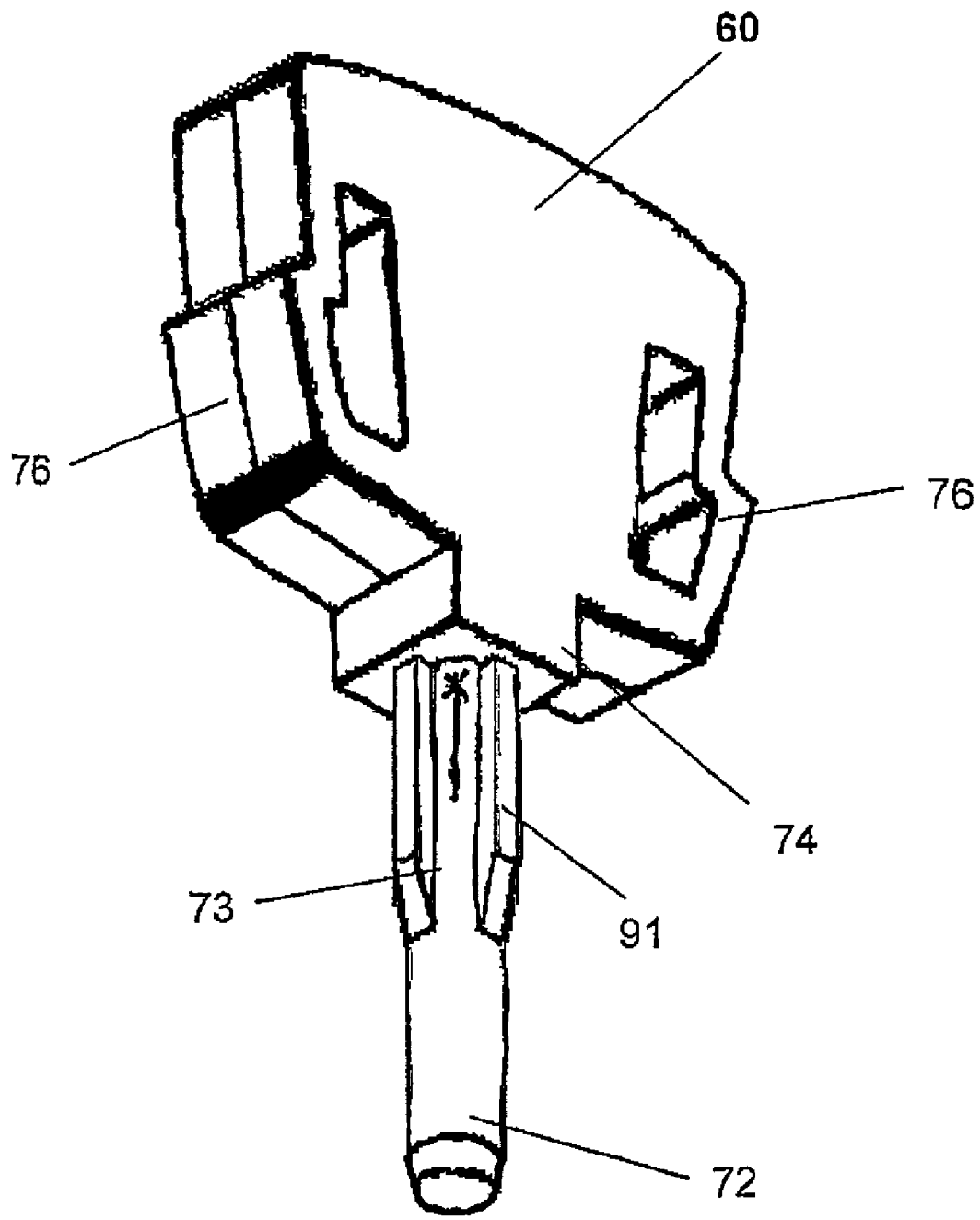
FIG. 6 is a perspective view of the stopper shown in FIGS. 2-5.
Figure 7:
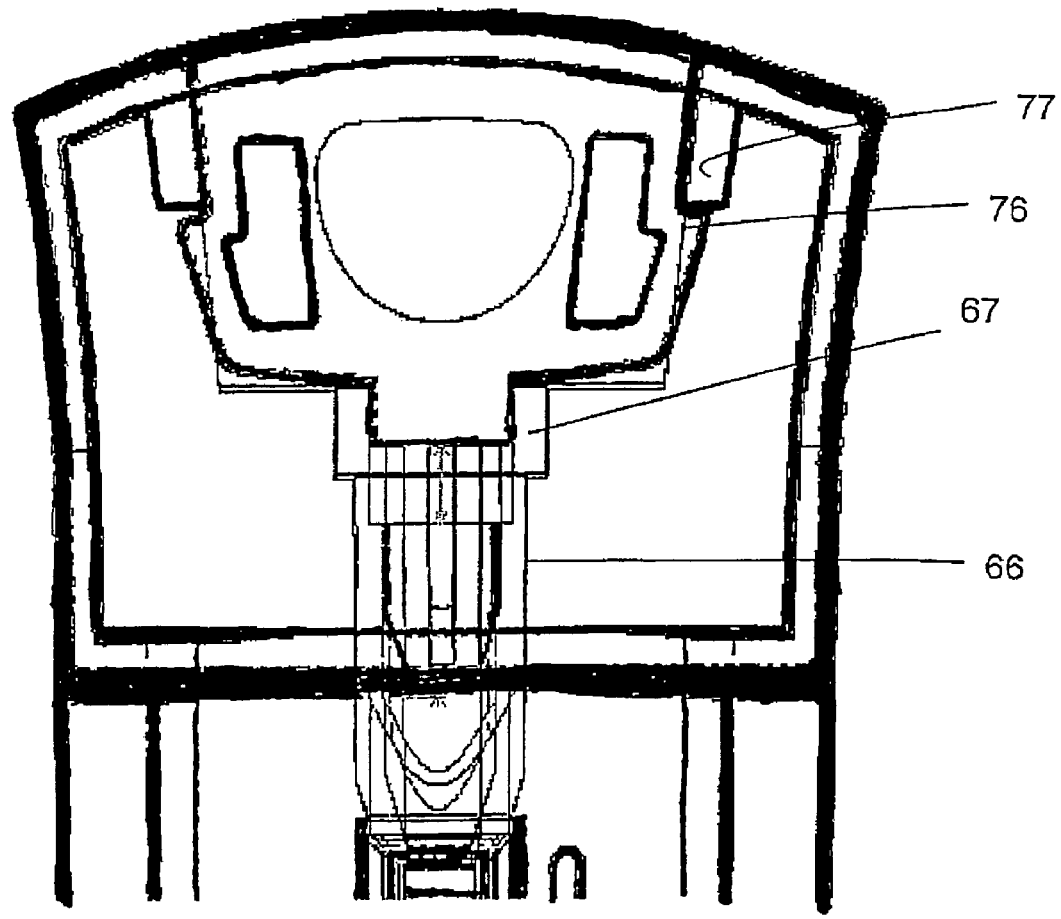
FIG. 7 is an enlarged fragmentary sectional view of the cartridge with the stopper operatively engaged with the body of the cartridge.

Further displacement of the stopper 60 allows the plug 74 at the proximal end of the stem 73 to engage in the enlarged mouth 67 of the vestibule and affect a second seal closing the upper end of the vestibule. As shown in FIGS. 6 and 7, the plug 74 is a rectangular block to mate with the enlarged mouth 67, which is in the form of a socket having a complementary rectangular form. The block 74 is of the same plastic material as the probe 72 having sufficient resiliency to effect a good seal with the enlarged mouth 67 when engaged as shown in FIG. 5C. The displacement of the plug 74 in the enlarged mouth 67 does not substantially increase the air pressure above the fill line 87.

The distance between the top of the cylindrical channel 89 of the inlet 65 and the bottom of the socket forming the enlarged mouth 67 is less than the distance between the tip of the probe 72 and the bottom of the plug 74 so that there is assurance that the probe enters into the channel 89 before the plug 74 seats against the bottom of the socket. This arrangement insures avoidance of any substantial pressure build-up in the vestibule 66. It is noted that the stem 73 has ribs 91 spaced circumferentially there around so that the space between the ribs provides an adequate space to accommodate the buffer solution displaced during the penetration of the probe into the cylindrical portion 89 of the inlet.

With the flexible walls engaging the keeper element 77 to keep the stopper in place, air is confined within the vestibule 66 between the first and second seals, and the cartridge may be manipulated without fear of air bubbles or the like interfering with the optical analysis of the liquid in the test chamber 63. After being filled and capped, the cartridge may be reoriented so that its longitudinal axis is horizontal for analysis in the detecting apparatus, as described above and illustrated in FIGS. 1 to 4, since the test chamber 63 is completely filled with liquid, it may be manipulated into other orientations, as may be required by the detecting apparatus chosen by the analyst. Any buffer solution, which is in contact with the test liquid is retained within the cartridge, either in the test chamber 63 or within the vestibule 66, and there is little danger of loss of any significant part of the test liquid. The buffer solution, which overlies the test liquid in the cartridge during the filling operation, assures minimal exposure of the test liquid to air and a diminished risk of deterioration or contamination of the test liquid.

While particular embodiments of the present invention have been herein illustrated and described, it is not intended to limit the invention to such disclosure, and many changes and modifications can be envisioned therein that may be made within the scope of the following claims.

What is claimed is:

1. An improved stopper having a probe on a projecting stem of said stopper, said probe forming a first seal adapted to sealingly seat in an inlet and close the same, said first seal precluding air entrapment within a test chamber upon being seated in said inlet, said probe having a distal end adapted to enter said inlet of said test chamber below an established fill level before said first seal closes said inlet, said distal end having a thickness sufficient to displace liquid upwardly through said inlet and position the surface of said fluid sample in a vestibule prior to said first seal closing said inlet and a plug on said projecting stem of said stopper proximal to said probe, said plug having a position along said projecting stem such that said vestibule remains open to an environment until after closing of said inlet by said probe then said plug engages with an enlarged mouth on said vestibule effecting a second seal to close the upper end of vestibule, wherein the improvement comprises:
   a. a single elastomer where the probe, the plug, and a stopper handhold are composed of said single elastomer; and
   b. a locking mechanism to engage with keeper elements on a cartridge, said mechanism having flexible walls on each side of said stopper handhold such that when said second seal closes the vestibule said flexible walls are compressed until they snap outwardly and allow said stopper to lock into place, said locking mechanism resists disengagement by twisting.

2. A stopper according to claim 1 wherein said elastomer has a durometer value in the range of approximately 60 to 100.

3. A stopper according to claim 1 wherein said elastomer has a durometer value in the range of approximately 80 to 90.

4. A stopper according to claim 1 wherein said elastomer has a durometer value of about 90.

* * * * *